US00PP30939P3

(12) United States Plant Patent
van Rosmalen

(10) Patent No.: US PP30,939 P3
(45) Date of Patent: Oct. 15, 2019

(54) *HYDRANGEA* PLANT NAMED 'HORE0031'

(50) Latin Name: *Hydrangea macrophylla*
Varietal Denomination: HORE0031

(71) Applicant: Nick van Rosmalen, Velp (NL)

(72) Inventor: Nick van Rosmalen, Velp (NL)

( * ) Notice: Subject to any disclaimer, the term of this patent is extended or adjusted under 35 U.S.C. 154(b) by 0 days.

(21) Appl. No.: 16/350,098

(22) Filed: Sep. 25, 2018

(65) Prior Publication Data

US 2019/0104664 P1 Apr. 4, 2019

Related U.S. Application Data

(60) Provisional application No. 62/606,622, filed on Sep. 29, 2017.

(51) Int. Cl.
*A01H 5/02* (2018.01)
*A01H 6/48* (2018.01)

(52) U.S. Cl.
USPC ..... Plt./250
CPC ..... *A01H 6/48* (2018.05)

(58) Field of Classification Search
USPC ..... Plt./250
CPC ..... A01H 5/02; A01H 6/48
See application file for complete search history.

(56) References Cited

PUBLICATIONS

PLUTO Plant Variety Database Apr. 11, 2019.*

* cited by examiner

*Primary Examiner* — Annette H Para
(74) *Attorney, Agent, or Firm* — C. A. Whealy

(57) ABSTRACT

A new and distinct cultivar of *Hydrangea* plant named 'HORE0031', characterized by its compact, upright and mounded plant habit; moderately vigorous to vigorous growth habit and moderate growth rate; freely branching habit with strong and sturdy stems; freely and uniformly flowering habit; mophead-type inflorescences with numerous light red purple-colored sterile flowers that become darker red purple with development; and good postproduction longevity.

3 Drawing Sheets

Botanical designation: *Hydrangea macrophylla.*
Cultivar denomination: 'HORE0031'.

BACKGROUND OF THE INVENTION

The present invention relates to a new and distinct cultivar of *Hydrangea* plant, botanically known as *Hydrangea macrophylla*, commercially referred to as a mophead-type *Hydrangea* and hereinafter referred to by the name 'HORE0031'.

The new *Hydrangea* plant is a product of a planned breeding program conducted by the Inventor in Velp and Reeuwijk, The Netherlands. The objective of the breeding program was to create new compact and freely-branching *Hydrangea* plants with strong sturdy stems, large inflorescences with numerous attractive sterile flowers and good postproduction longevity.

The new *Hydrangea* plant originated from a cross-pollination made by the Inventor in July, 2011 in Velp, The Netherlands, of a proprietary selection of *Hydrangea macrophylla* identified as code number 12-00-04, not patented, as the female, or seed, parent with a proprietary selection of *Hydrangea macrophylla* identified as code number 12-00-73, not patented, as the male, or pollen, parent. The new *Hydrangea* plant was discovered and selected by the Inventor as a single flowering plant from within the progeny of the stated cross-pollination in a controlled greenhouse environment in Reeuwijk, The Netherlands in June, 2013.

Asexual reproduction of the new *Hydrangea* plant by vegetative tip cuttings in a controlled environment in Reeuwijk, The Netherlands since August, 2015 has shown that the unique features of this new *Hydrangea* plant are stable and reproduced true to type in successive generations.

SUMMARY OF THE INVENTION

Plants of the new *Hydrangea* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'HORE0031'. These characteristics in combination distinguish 'HORE0031' as a new and distinct *Hydrangea* plant:

1. Compact, upright and mounded plant habit.
2. Moderately vigorous to vigorous growth habit and moderate growth rate.
3. Freely branching habit with strong and sturdy stems.
4. Freely and uniformly flowering habit.
5. Mophead-type inflorescences with numerous light red purple-colored sterile flowers that become darker red purple with development.
6. Good postproduction longevity.

Plants of the new *Hydrangea* can be compared to plants of the female parent selection. Plants of the new *Hydrangea* differ primarily from plants of the female parent selection in the following characteristics:

1. Plants of the new *Hydrangea* have darker green-colored leaves than plants of the female parent selection.
2. Plants of the new *Hydrangea* have lighter red purple-colored sterile flower sepals than plants of the female parent selection.

Plants of the new *Hydrangea* can be compared to plants of the male parent selection. Plants of the new *Hydrangea* differ primarily from plants of the male parent selection in the following characteristics:

1. Plants of the new *Hydrangea* are more freely flowering than plants of the male parent selection.
2. Sterile flower sepals of plants of the new *Hydrangea* are light red purple in color whereas sterile flower sepals of the male parent selection are white in color.

Plants of the new *Hydrangea* can be compared to plants of the *Hydrangea macrophylla* 'Hopaline', not patented. In side-by-side comparisons, plants of the new *Hydrangea* differ primarily from plants of 'Hopaline' in the following characteristics:

1. Plants of the new *Hydrangea* have stronger stems than plants of 'Hopaline'.
2. Leaves of plants of the new *Hydrangea* are darker green in color than leaves of plants of 'Hopaline'.
3. Sterile flower sepals of plants of the new *Hydrangea* are darker red purple in color than sterile flower sepals of plants of 'Hopaline'.

BRIEF DESCRIPTION OF THE PHOTOGRAPHS

The accompanying colored photographs illustrate the unique appearance of the new *Hydrangea* plant showing the colors as true as it is reasonably possible to obtain in colored reproductions of this type. Colors in the photographs may differ from the color values cited in the detailed botanical description which accurately describe the colors of the new *Hydrangea* plant.

The photograph on the first sheet is a side perspective view of a typical flowering plant of 'HORE0031' during an early stage of development.

The photograph at the top of the second sheet is a close-up view of a typical developing inflorescence of 'HORE0031'.

The photograph at the bottom of the second sheet is a close-up view of a typical leaf of 'HORE0031'.

The photograph on the third sheet is a side perspective view of a typical flowering plant of 'HORE0031' at a stage of full development.

DETAILED BOTANICAL DESCRIPTION

Plants used in the aforementioned photographs and in the following description were grown during the summer in 13-cm containers in a glass-covered greenhouse in Reeuwijk, The Netherlands and under cultural practices typical of commercial *Hydrangea* production. During the production of the plants, day temperatures ranged from about 20° C. to 35° C. and night temperatures ranged from about averaged 12° C. to 22° C. Plants of the new *Hydrangea* were two years old when the photographs and description were taken. Plants of the new *Hydrangea* are typically not treated with aluminum sulfate to "blue" the inflorescences. In the following description, color references are made to The Royal Horticultural Society Colour Chart, 2015 Edition, except where general terms of ordinary dictionary significance are used.

Botanical description: *Hydrangea macrophylla* 'HORE0031'.

Parentage:

*Female, or seed, parent*.—Proprietary selection of *Hydrangea macrophylla* identified as code number 12-00-04, not patented.

*Male, or pollen, parent*.—Proprietary selection of *Hydrangea macrophylla* identified as code number 12-00-73, not patented.

Propagation:

*Type cutting*.—By vegetative tip cuttings.

*Time to initiate roots, summer*.—About 16 days at temperatures about 20° C. to 30° C.

*Time to produce a rooted young plant, summer*.—About four months at temperatures about 20° C. to 30° C.

*Root description*.—Medium in thickness, fibrous; typically light brown in color, actual color of the roots is dependent on substrate composition, water quality, fertilizer type and formulation, substrate temperature and physiological age of roots.

*Rooting habit*.—Freely branching; dense.

Plant description:

*Plant and growth habit*.—Compact, upright and rounded plant habit; overall plant shape, broadly obovate; strong and sturdy stems; moderately vigorous to vigorous growth habit and moderate growth rate.

*Plant height*.—About 29.5 cm.

*Plant diameter or area of spread*.—About 44.6 cm.

Lateral branch description:

*Branching habit*.—Freely branching habit; when pinched, about eleven lateral branches develop per plant.

*Length*.—About 14.1 cm.

*Diameter*.—About 5 mm.

*Internode length*.—About 3.8 cm.

*Texture*.—Smooth, glabrous; fully developed, woody.

*Aspect*.—Upright to about 60° from vertical.

*Strength*.—Strong, sturdy.

*Color*.—When developing: Close to 145A. Developed: Close to 143A; when woody, close to 199C and 200A.

*Lenticels*.—Density: Medium. Size: About 1 mm by 0.75 mm. Color: Close to N186C.

Leaf description:

*Arrangement*.—Opposite, simple.

*Length*.—About 10.4 cm.

*Width*.—About 8.7 cm.

*Shape*.—Broadly ovate.

*Apex*.—Apiculate.

*Base*.—Truncate to cordate.

*Margin*.—Serrate.

*Texture, upper and lower surfaces*.—Smooth to slightly rugose, glabrous.

*Venation pattern*.—Pinnate.

*Color*.—Developing leaves, upper surface: Darker than 143A. Developing leaves, lower surface: Close to between 144A and 146B. Fully developed leaves, upper surface: Darker than between 139A and 147A; venation, close to 145A. Fully developed leaves, lower surface: Close to 147B; venation, close to 145A to 145B.

*Petioles*.—Length: About 1.7 cm. Diameter: About 3 mm to 4 mm. Texture and luster, upper and lower surfaces: Smooth, glabrous; slightly glossy. Color, upper and lower surfaces: Close to 144B.

Flower description:

*Flower type and habit*.—Showy sterile flowers and small inconspicuous fertile flowers arranged on mophead-type terminal panicles; panicles rounded and flattened globular in shape; flowers face upright to outwardly depending on their position in the inflorescence.

*Fragrance*.—None detected.

*Natural flowering season*.—Early flowering habit, plants begin flowering about three months after planting; flowering begins in the late spring and is continuous until late summer in Northern Europe.

*Flower longevity*.—Fertile flowers last about five days on the plant, fertile flowers not persistent; sterile flowers last about six weeks on the plant, sterile flowers persistent.

*Quantity of flowers*.—Freely flowering habit; about 35 fertile flowers per panicle and about 130 sterile flowers per panicle.

*Panicle height*.—About 10.6 cm.

*Panicle diameter*.—About 15.4 cm.

*Fertile flower buds*.—Length: About 4 mm. Diameter: About 4 mm. Shape: Broadly obovate. Color: Close to between 150D and 155A towards the base fading to close to N144D and at the base, close to 143A.

*Sterile flower buds*.—Length: About 6 mm. Diameter: About 6 mm. Shape: Cup-shaped. Color: Close to 145D.

*Fertile flower diameter*.—About 7 mm.

*Fertile flower depth* (*height*).—About 6 mm.

*Sterile flower diameter*.—About 3.9 cm.

*Sterile flower depth* (*height*).—About 1.6 cm.

*Petals, fertile flowers*.—Quantity and arrangement: Five in a single whorl. Length: About 3 mm. Width: About 1.75 mm. Shape: Ovate, concave. Apex: Acute. Base: Cuneate. Margin: Entire. Texture and luster, upper surface: Smooth, glabrous; slightly glossy. Texture and luster, lower surface: Smooth, glabrous; matte. Color: When opening and fully opened, upper surface: Close to NN155D. When opening and fully opened, lower surface: Close to NN155D.

*Petals, sterile flowers*.—Quantity and arrangement: Four in a single whorl. Length: About 3 mm. Width: About 1.75 mm. Shape: Ovate, concave. Apex: Acute. Base: Cuneate. Margin: Entire. Texture and luster, upper surface: Smooth, glabrous; slightly glossy. Texture and luster, lower surface: Smooth, glabrous; matte. Color: When opening and fully opened, upper surface: Close to NN155D. When opening and fully opened, lower surface: Close to NN155D.

*Sepals, fertile flowers*.—Quantity and arrangement: Five in a single whorl. Length: About 2.5 mm. Width: About 2 mm. Shape: Broadly ovate. Apex: Acute. Base: Broadly cuneate. Margin: Entire. Texture and luster, upper and lower surfaces: Smooth, glabrous; matte. Color: When opening, upper surface: Close to 143B fading towards the base to close to N144D. When opening, lower surface: Close to 143A fading towards the base to close to N144D. Fully opened, upper and lower surfaces: Close to 144A fading towards the base to close to 145C.

*Sepals, sterile flowers*.—Quantity and arrangement: Four or occasionally five in a single whorl. Length: About 2.1 cm. Width: About 2.4 cm. Shape: Broadly ovate to roughly deltoid. Apex: Broadly acutely obtuse. Base: Broadly cuneate. Margin: Entire, occasionally with one or two small teeth. Texture and luster, upper and lower surfaces: Smooth, glabrous; matte. Color: When opening, upper surface: Close to NN155C fading towards the apex to close to 145D, 150D and lighter than 150D; base tinged with close to 65B to 65C. When opening, lower surface: Close to between 69D and NN155C fading towards the apex to close to 145D, 150D and lighter than 150D. Fully opened, upper and lower surfaces: Close to NN155A to NN155B fading towards the apex to close to 145B; base, strongly tinged with close to 65A to 65C; color becoming predominantly more red purple with development.

*Pedicels, fertile flowers*.—Length: About 3 mm. Diameter: About 1 mm. Strength: Moderately strong. Aspect: About 10° from vertical. Texture and luster: Sparsely pubescent; matte. Color: Close to 145D.

*Pedicels, sterile flowers*.—Length: About 3.1 cm. Diameter: About 2 mm. Strength: Moderately strong. Aspect: About 45° from branch axis. Texture and luster: Pubescent; matte. Color: Close to 157D.

*Reproductive organs, fertile flowers*.—Stamens: Quantity per flower: About ten. Filament length: About 1.5 mm. Filament color: Close to NN155C. Anther length: About 0.75 mm. Anther shape: Broadly oblong. Anther color: Close to 155C. Pollen amount: Moderate. Pollen color: Close to 158D. Pistils: Pistil quantity per flower: Three. Pistil length: About 1 mm. Stigma shape: Club-shaped. Stigma color: Close to 157D. Style length: About 0.5 mm. Style color: Close to 145D. Ovary color: Close to 145D.

*Reproductive organs, sterile flowers*.—Stamens: Quantity per flower: About ten. Filament length: About 1.5 mm. Filament color: Close to NN155C. Anther length: About 0.75 mm. Anther shape: Broadly oblong. Anther color: Close to 155C. Pollen amount: Moderate. Pollen color: Close to 158D. Pistils: Pistil quantity per flower: Three. Pistil length: About 1 mm. Stigma shape: Club-shaped. Stigma color: Close to 157D. Style length: About 0.5 mm. Style color: Close to 145D. Ovary color: Close to 145D.

*Seeds*.—To date, seed production has not been observed on plants of the new *Hydrangea*.

Pathogen & pest resistance: To date, under commercial production conditions, plants of the new *Hydrangea* have not been observed to be resistant to pathogens and pests common to *Hydrangea* plants.

Temperature tolerance: Plants of the new *Hydrangea* have been shown to be suitable for USDA Hardiness Zones 5 through 9.

It is claimed:

1. A new and distinct *Hydrangea* plant named 'HORE0031' as illustrated and described.

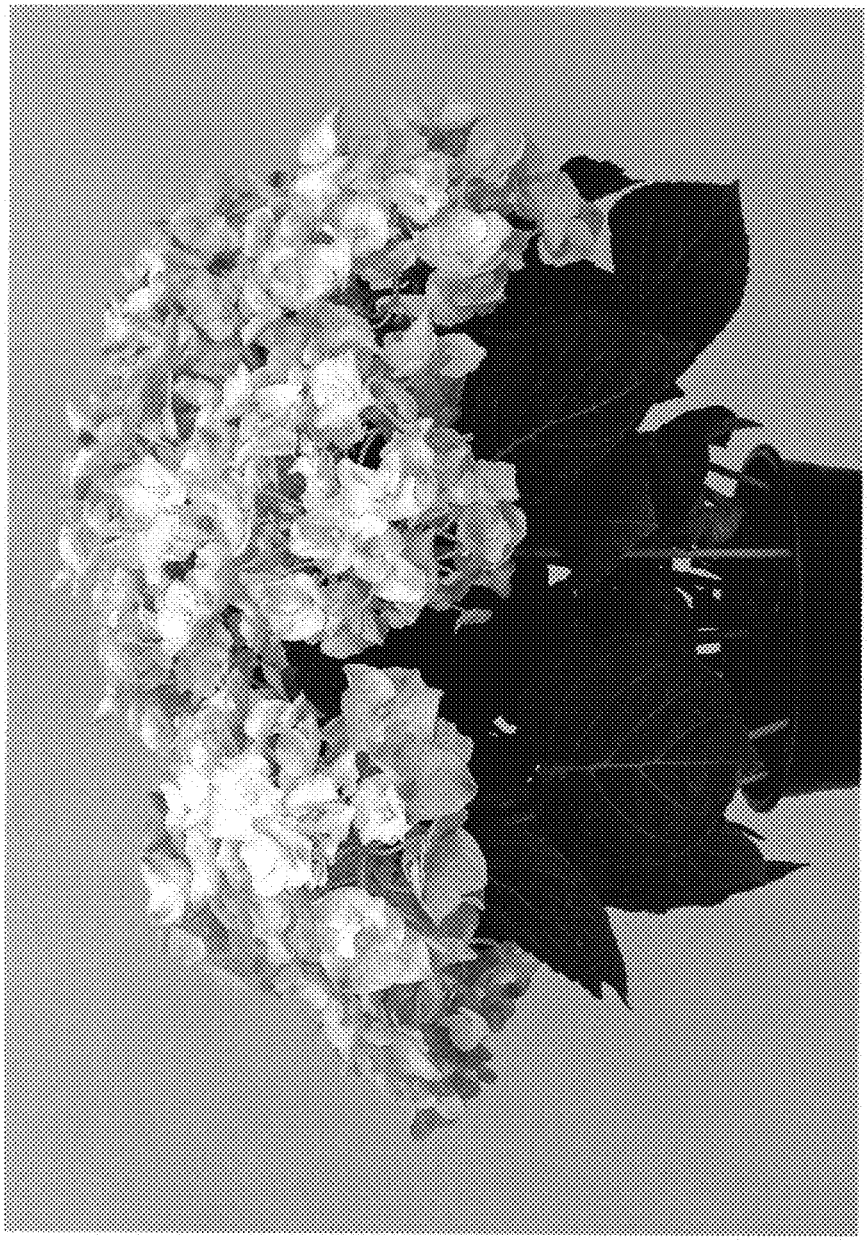

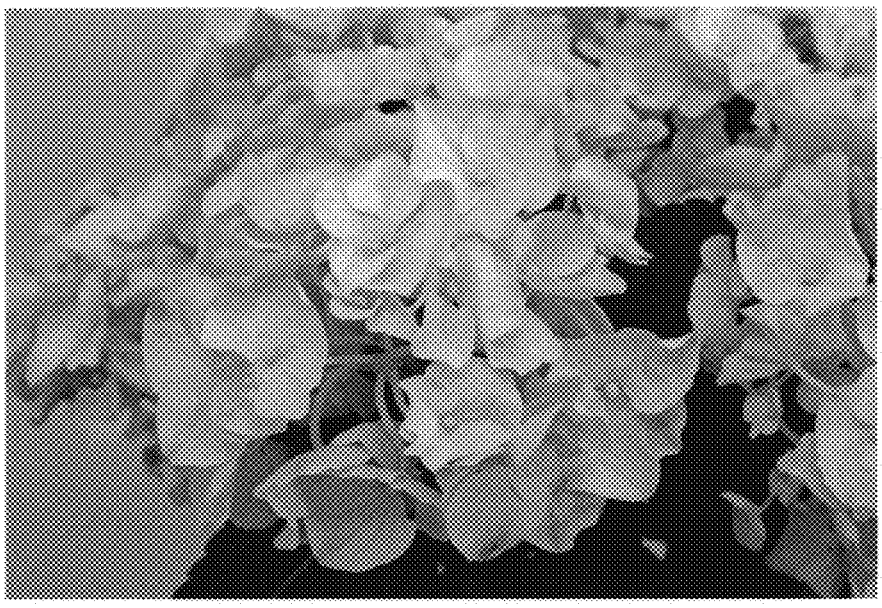
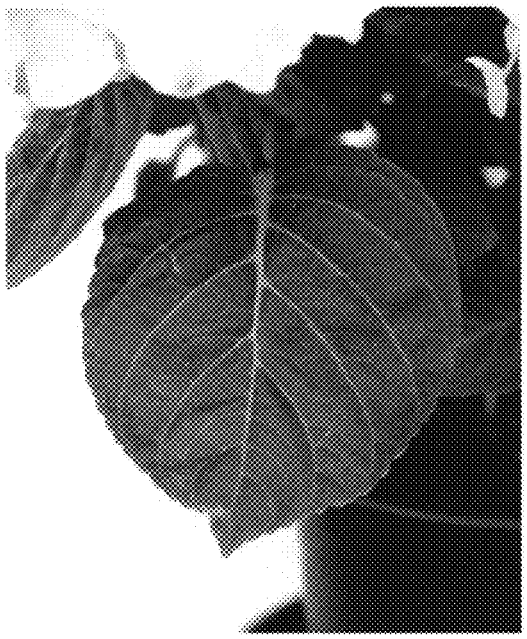

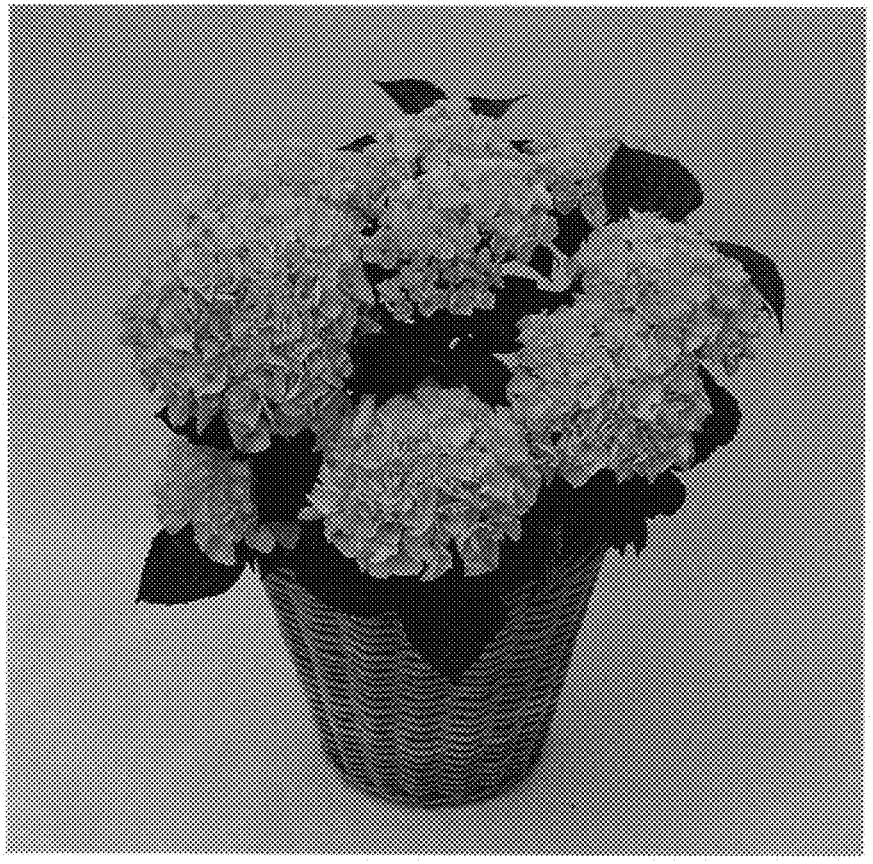

* * * * *